(12) United States Patent
Hinze et al.

(10) Patent No.: US 7,288,560 B2
(45) Date of Patent: Oct. 30, 2007

(54) SPIROCYCLIC CYCLOHEXANE DERIVATIVES

(75) Inventors: Claudia Hinze, Aachen (DE); Bernd Sundermann, Aachen (DE); Hans Schick, Berlin (DE); Birgitta Henkel, Berlin (DE)

(73) Assignee: Gruenenthal GmbH, Aachen (DE)

( * ) Notice: Subject to any disclaimer, the term of this patent is extended or adjusted under 35 U.S.C. 154(b) by 180 days.

(21) Appl. No.: 11/019,416

(22) Filed: Dec. 23, 2004

(65) Prior Publication Data
US 2005/0187281 A1    Aug. 25, 2005

(30) Foreign Application Priority Data
Dec. 23, 2003  (DE)  ................. 103 60 793

(51) Int. Cl.
*A61K 31/407* (2006.01)
*C07D 491/052* (2006.01)

(52) U.S. Cl. .......... 514/409; 548/407; 549/13; 549/43; 549/385; 546/15; 546/18; 514/278; 514/411; 514/437; 514/443; 514/454

(58) Field of Classification Search ........... 514/409, 514/278, 411, 437, 443, 454; 548/407; 549/13, 549/43, 385; 546/15, 18
See application file for complete search history.

(56) References Cited

OTHER PUBLICATIONS

Miyuki Nishi et al., "Unrestrained Nociceptive Response and Disregulation of Hearing Ability in Mice Lacking the Nociceptin/OrphaninFQ Receptor," The EMBO Journal, 1997, pp. 1858-1864, vol. 16, No. 8, Oxford University Press.

Ali Ardati et al., "Interaction of [$^3$H]Orphanin FQ and $^{125}$I-Tyr14-Orphanin FQ with the Orphanin FQ Receptor: Kinetics and Modulation by Cations and Guanine Nucleotides," Molecular Pharmacology, 1997, pp. 816-824, 51, The American Society for Pharmacology and Experimental Therapeutics.

Girolamo Calo et al., "Pharmacology of Nociceptin and its Receptor: A Novel Therapeutic Target," British Journal of Pharmacology, 2000, pp. 1261-1283, 129, Macmillan Publishers Ltd.

Toshiya Manabe et al., "Facilitation of Long-Term Potentiation and Memory in Mice Lacking Nociceptin Receptors", Letters To Nature, Aug. 6, 1998, pp. 577-581, vol. 394, Macmillan Publishers Ltd.

Elmar Friderichs, "Opioids", pp. 127-145, chapter 3.1.

Claudia Pütz, "Further Opioid Receptors" pp. 455-476, chapter 3.4.

Petrus J. Pauwels, et al., "3H Batrachotoxinin A 20-a-Benzoate Binding to Sodium Channels in Rat Brain: Characterization and Pharmacological Significance" European Journal of Pharmacology, 1986, pp. 291-298, vol. 124, Elsevier Science Publishers B.V.

By E. G. Gray, et al., "The Isolation of Nerve Endings From Brain: An Electron-Microscopic Study of Cell Fragments Derived By Homogenization and Centrifugation", Journal of Anatomy, 1996, pp. 79-89, vol. 96, Part 1.

*Primary Examiner*—Charanjit S. Aulakh
(74) *Attorney, Agent, or Firm*—Crowell & Moring LLP

(57) ABSTRACT

The present invention relates to spirocyclic cyclohexane compounds, to methods for their production, to pharmaceutical compositions containing these compounds, to methods of treatment using such compounds and to the use of such spirocyclic cyclohexarie compounds for producing pharmaceutical compositions.

31 Claims, No Drawings

SPIROCYCLIC CYCLOHEXANE DERIVATIVES

CROSS-REFERENCE TO RELATED APPLICATIONS

This application claims the priority of German Patent Document No. 103 60 793.5, filed Dec. 23, 2003, the disclosure of which is expressly incorporated by reference herein.

FIELD OF THE INVENTION

The present invention relates to spirocyclic cyclohexane derivatives, to methods for their production, to pharmaceutical compositions containing these compounds, to method of treatment using these compounds and to the use of spirocyclic cyclohexane derivatives for producing pharmaceutical compositions.

BACKGROUND OF THE INVENTION

The treatment of chronic and non-chronic pain conditions has great importance in medicine. There is a worldwide need for effective methods of treating pain. The urgent need for patient-friendly and purposeful treatment of chronic and non-chronic pain conditions, especially the successful and satisfactory treatment of pain for the patient, is documented in the large number of scientific papers which have recently appeared in the field of applied analgesics and fundamental research work on nociception.

Conventional μ-opioids such as morphine are very effective in the therapy of strong to very strong pain and are of great importance for the treatment of pain. However, it may be advantageous if, in addition to the μ-opioid receptor, other opioid receptors (δ, κ, ORL-1) are influenced, as the pure μ-opioids also have undesirable side effects such as obstipation and respiratory depression, and may also lead to dependency. The opioid receptors δ, κ and ORL-1 are involved in the pain states (Opioids: Introduction, p. 127-150, Further Opioid Receptors, 455-476 in: Analgesics—From Chemistry and Pharmacology to Clinical Application, Wiley VCH 2002).

The ORL1 receptor is also involved in the regulation of further physiological and pathophysiological processes. These include inter alia learning and memory (Manabe et al., Nature, 394, 1997, p. 577-581), hearing capacity (Nishi et al., EMBO J., 16, 1997, p. 1858-1864) and numerous further processes. A synopsis by Calo et al. (Br. J. Pharmacol. 129, 2000, 1261-1283) gives an overview of the indications or biological procedures, in which the ORL1-receptor plays a part or could very likely play a part. Mentioned inter alia are: analgesics; stimulation and regulation of nutrient absorption; effect on μ-agonists such as morphine; treatment of withdrawal symptoms; reduction of the addiction potential of opioids; anxiolysis; modulation of motor activity; memory disorders; epilepsy; modulation of neurotransmitter release, in particular of glutamate, serotonin and dopamine, and therefore neurodegenerative diseases; influencing the cardiovascular system; triggering an erection; diuresis; anti-natriuresis; electrolyte balance; arterial blood pressure; water retention disorders; intestinal motility (diarrhea); relaxation of the respiratory tract; and micturition reflex (urinary incontinence). The use of agonists and antagonists as anoretics, analgesics (also when administered with opioids) or nootropics is also discussed.

An object of the present invention is to provide pharmaceutical compositions which act on the opioid receptor system and are thus suitable for pharmaceutical compositions, in particular for the treatment of the various diseases associated with this system according to the prior art and for use in the indications mentioned therein.

The invention therefore relates to spirocyclic cyclohexane derivatives of general formula I,

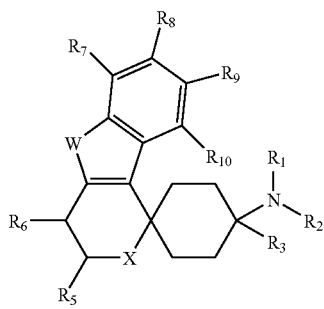

wherein $R^1$ and $R^2$ independently of one another represent H; CHO; respectively saturated or unsaturated, branched or unbranched, singly or multiply substituted or unsubstituted $C_{1-5}$ alkyl; respectively saturated or unsaturated, singly or multiply substituted or unsubstituted $C_{3-8}$ cycloalkyl; or respectively singly or multiply substituted or unsubstituted aryl, $C_{3-8}$ cycloalkyl or heteroaryl bound by $C_{1-3}$ alkyl or the radicals $R^1$ and $R^2$ together form $CH_2H_2OCH_2CH_2$, $CH_2CH_2NR^{11}CH_2CH_2$ or $(CH_2)_{3-6}$, wherein $R^{11}$ represents H; respectively saturated or unsaturated, branched or unbranched, singly or multiply substituted or unsubstituted $C_{1-5}$ alkyl; respectively saturated or unsaturated, singly or multiply substituted or unsubstituted $C_{3-8}$ cycloalkyl; respectively singly or multiply substituted or unsubstituted aryl or heteroaryl; or respectively singly or multiply substituted or unsubstituted aryl, $C_{3-8}$ cycloalkyl or heteroaryl bound by $C_{1-3}$ alkyl;

$R^3$ represents respectively saturated or unsaturated, branched or unbranched, singly or multiply substituted or unsubstituted $C_{1-5}$ alkyl; respectively saturated or unsaturated, singly or multiply substituted or unsubstituted $C_{3-8}$ cycloalkyl; respectively unsubstituted or singly or multiply substituted aryl or heteroaryl; or respectively unsubstituted or singly or multiply substituted aryl, heteroaryl or $C_{3-8}$ cycloalkyl bound by $C_{1-3}$ alkyl group;

W represents $NR^4$, O or S and $R^4$ represents H; saturated or unsaturated, branched or unbranched, unsubstituted or singly or multiply substituted $C_{1-5}$ alkyl; respectively substituted or unsubstituted aryl or heteroaryl; respectively singly or multiply substituted or unsubstituted aryl, heteroaryl or cycloalkyl bound by a $C_{1-3}$ alkyl group; $COR^{12}$ or $SO_2R^{12}$, wherein $R^{12}$ represents H; respectively saturated or unsaturated, branched or unbranched, singly or multiply substituted or unsubstituted $C_{1-5}$ alkyl; respectively saturated or unsaturated, singly or multiply substituted or unsubstituted $C_{3-8}$ cycloalkyl; respectively singly or multiply substituted or unsubstituted aryl or heteroaryl; or respectively singly or multiply substituted or unsubstituted aryl, $C_{3-8}$ cycloalkyl or heteroaryl bound by $C_{1-3}$ alkyl; $OR^{13}$ or $NR^{14}R^{15}$;

$R^5$ represents =O; H; $COOR^{13}$, $CONR^{13}$, $OR^{13}$; saturated or unsaturated, branched or unbranched, singly or multiply substituted or unsubstituted $C_{1-5}$ alkyl; saturated or unsaturated, unsubstituted or singly or multiply substituted $C_{3-8}$ cycloalkyl; unsubstituted or singly or multiply substituted aryl or heteroaryl; or unsubstituted or singly or multiply substituted aryl, $C_{3-8}$ cycloalkyl or heteroaryl bound by $C_{1-3}$ alkyl;

$R^6$ represents H; F, Cl, $NO_2$, $CF_3$, $OR^{13}$, $SR^{13}$, $SO_2R^{13}$, $SO_2R^{13}$, CN, $COOR^{13}$, $NR^{14}R^{15}$; saturated or unsaturated, branched or unbranched, unsubstituted or singly or multiply substituted $C_{1-5}$ alkyl; saturated or unsaturated, unsubstituted or singly or multiply substituted $C_{3-8}$ cycloalkyl; unsubstituted or singly or multiply substituted aryl or heteroaryl; or unsubstituted or singly or multiply substituted aryl, $C_{3-8}$ cycloalkyl or heteroaryl bound by $C_{1-3}$ alkyl;

or $R^5$ and $R^6$ together represent $(CH_2)_n$ where n=2, 3, 4, 5 or 6, wherein individual hydrogen atoms may also be replaced by F, Cl, Br, I, $NO_2$, $CF_3$, $OR^{13}$, CN or $C_{1-5}$ alkyl;

$R^7$, $R^8$, $R^9$ and $R^{10}$, independently of one another, represent H, F, Cl, Br, I, $NO_2$, $CF_3$, $OR^{13}$, $SR^{13}$, $SO_2R^{13}$, $SO_2OR^{13}$, CN, $COOR^{13}NR^{14}R^{15}$; unsubstituted or singly or multiply substituted $C_{1-5}$ alkyl, $C_{3-8}$ cycloalkyl; unsubstituted or singly or multiply substituted aryl or heteroaryl; or unsubstituted or singly or multiply substituted aryl, $C_{3-8}$ cycloalkyl or heteroaryl bound by $C_{1-3}$ alkyl;

wherein $R^{13}$ represents H; respectively saturated or unsaturated, branched or unbranched, unsubstituted or singly or multiply substituted $C_{1-5}$ alkyl; respectively saturated or unsaturated, unsubstituted or singly or multiply substituted $C_{3-8}$ cycloalkyl; unsubstituted or singly or multiply substituted aryl or heteroaryl; or unsubstituted or singly or multiply substituted aryl, $C_{3-8}$ cycloalkyl or heteroaryl bound by $C_{1-3}$ alkyl;

$R^{14}$ and $R^{15}$ independently of one another represent H; respectively saturated or unsaturated, branched or unbranched, unsubstituted or singly or multiply substituted $C_{1-5}$ alkyl; respectively saturated or unsaturated, unsubstituted or singly or multiply substituted $C_{3-8}$ cycloalkyl; unsubstituted or singly or multiply substituted aryl or heteroaryl; or unsubstituted or singly or multiply substituted aryl, $C_{3-8}$ cycloalkyl or heteroaryl bound by $C_{1-3}$ alkyl;

or $R^{14}$ and $R^{15}$ together form $CH_2CH_2OCH_2CH_2$, $CH_2CH_2NR^{16}CH_2CH_2$ or $(CH_2)_{3-6}$;

wherein $R^{16}$ represents H; saturated or unsaturated, branched or unbranched, unsubstituted or singly or multiply substituted $C_{1-5}$ alkyl;

X represents O, S, SO, $SO_2$ or $NR^{17}$;

$R^{17}$ represents H; $C_{1-5}$ alkyl, saturated or unsaturated, branched or unbranched; $COR^{12}$ or $SO_2R^{12}$;

in the form of the racemate; the enantiomers, diastereomers, mixtures of the enantiomers or diastereomers or an individual enantiomer or diastereomer; the bases and/or salts of physiologically acceptable acids or cations.

When combining various radicals, for example $R^7$, $R^8$, $R^9$ and $R^{10}$, and when combining radicals on their substituents, such as $OR^{13}$, $SR^{13}$, $SO_2R^{13}$ or $COOR^{13}$, a substituent, for example $R^{13}$, can assume different meanings for two or more radicals, for example $R^7$, $R^8$, $R^9$ and $R^{10}$, within a substance.

The compounds according to the invention exhibit good binding to the μ-receptor and also to other opioid receptors. Surprisingly, it has been found that the substances also have an affinity for binding site 2 of the sodium channel (BTX binding).

As a result, the compound class of general formula I is also suitable for use as a local anaesthetic.

The terms "$C_{1-5}$ alkyl" and "$C_{1-3}$ alkyl", according to the invention, include acyclic saturated or unsaturated hydrocarbon radicals, which may be branched or straight-chained and unsubstituted or singly or multiply substituted, with 1, 2, 3, 4 or 5 C atoms or 1, 2 or 3 C atoms, i.e. $C_{1-5}$ alkanyls, $C_{2-5}$ alkenyls and $C_{2-5}$ alkinyls or $C_{1-3}$ alkanyls, $C_{2-3}$ alkenyls and $C_{2-3}$ alkinyls. Alkenyls have at least one C—C double bond and alkinyls at least one C—C treble bond. Alkyl is advantageously selected from the group comprising methyl, ethyl, n-propyl, 2-propyl, n-butyl, iso-butyl, sec.-butyl, tertiary-butyl, n-pentyl, iso-pentyl, neo-pentyl, n-hexyl, 2-hexyl; ethylenyl (vinyl), ethinyl, propenyl (—$CH_2CH=CH_2$, —CH=CH—$CH_3$, —C(=$CH_2$)—$CH_3$), propinyl (—CH—C≡CH, —C≡C—$CH_3$), 1,1-dimethylethyl, 1,1-dimethylpropyl, butenyl, butinyl, pentenyl and pentinyl.

For the purposes of this invention the term "cycloalkyl" or "$C_{3-8}$ cycloalkyl" denotes cyclic hydrocarbons with 3, 4, 5, 6, 7 or 8 carbon atoms, wherein the hydrocarbons may be saturated or unsaturated (but not aromatic), unsubstituted or singly or multiply substituted. With respect to cycloalkyl, the term also comprises saturated or unsaturated (but not aromatic) cycloalkyls, in which one or two carbon atoms are replaced by a heteroatom, S, N or O. $C_{3-8}$ cycloalkyl is advantageously selected from the group comprising cyclopropyl, cyclobutyl, cyclopentane, cyclohexyl, cycloheptyl, cyclooctyl, cyclopentenyl, cyclohexenyl, cycloheptenyl and cyclooctenyl, and also tetrahydropyranyl, dioxanyl, dioxolanyl, morpholinyl, piperidinyl, piperazinyl, pyrazolinonyl and pyrrolidinyl.

The term $(CH_2)_{3-6}$ is taken to mean —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and $CH_2$—$CH_2$—$CH_2$—$CH_2$—$CH_2$—$CH_2$.

The term "aryl", according to this invention, denotes carbocyclic ring systems comprising at least one aromatic ring, but without a heteroatom in only one of the rings, inter alia phenyls, naphthyls and phenanthrenyls, fluoranthenyls, fluorenyls, indanyls and tetralinyls. The aryl radicals can also be condensed with further saturated, (partially) unsaturated or aromatic ring systems. Each aryl radical can be unsubstituted or singly or multiply substituted, wherein the aryl substituents may be the same or different and in any desired or possible position of the aryl. Phenyl- or naphthyl radicals are particularly advantageous.

The term "heteroaryl" represents a 5-, 6- or 7-membered cyclic aromatic radical, which contains at least 1, optionally also 2, 3, 4 or 5 heteroatoms, wherein the heteroatoms may be the same or different and the heterocycle unsubstituted or singly or multiply substituted; in the case of substitution on the heterocycle, the substituents may be the same or different and in any desired, possible position of the heteroaryl. The heterocycle may also be part of a bicyclic or polycyclic system. Preferred heteroatoms include nitrogen, oxygen and sulphur. It is preferred that the heteroaryl radical is selected from the group comprising pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phtalazinyl, pyrazolyl, imidazolyl, thiazolyl, oxazolyl, isoxazoyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, wherein the bond to the compounds of general structure I may be effected by any desired, possible ring member of the heteroaryl radical.

In connection with "alkyl", the term "substituted" according to this invention is taken to mean the substitution of one or more hydrogen radicals by F, Cl, Br, I, —CN, $NH_2$, NH-alkyl, NH-aryl, NH-heteroaryl, NH-cycloalkyl, NH-alkyl aryl, NH-alkyl heteroaryl, NH-alkyl OH, $N(alkyl)_2$, $N(alkyl\ aryl)_2$, $N(alkyl\ heteroaryl)_2$, $N(cycloalkyl)_2$, $N(alkyl\ OH)_2$, $NO_2$, SH, S-alkyl, S-aryl, S-heteroaryl, S-alkyl aryl, S-alkyl heteroaryl, S-cycloalkyl, S-alkyl OH, S-alkyl SH, OH, O-alkyl, O-aryl, O-heteroaryl, O-alkyl aryl, O-alkyl heteroaryl, O-cycloalkyl, O-alkyl OH, CHO, $C(=O)C_{1-6}$ alkyl, $C(=S)C_{1-6}$-alkyl, $C(=O)$aryl, $C(=S)$aryl, $C(=O)C_{1-6}$ alkyl aryl, $C(=S)C_{1-6}$ alkyl aryl, $C(=O)$-heteroaryl, $C(=S)$-heteroaryl, $C(=O)$-cycloalkyl, $C(=S)$-cycloalkyl, $CO_2H$, $CO_2$ alkyl, $CO_2$-alkyl aryl, $C(=O)NH_2$, $C(=O)$NH-alkyl, $C(=O)$NH-aryl, $C(=O)$NH-cycloalkyl, $C(=O)N(alkyl)_2$, $C(=O)N(alkyl\ aryl)_2$, $C(=O)N(alkyl\ heteroaryl)_2$, $C(=O)N(cycloalkyl)_2$, SO-alkyl, $SO_2$-alkyl, $SO_2NH_2$, $SO_3H$, $PO(O-C_{1-6}$-$alkyl)_2$, $Si(C_{1-6}alkyl)_3$, $Si(C_{3-8}\ cycloalkyl)_3$, $Si(CH_2-C_{3-8}\ cycloalkyl)_3$, $Si(phenyl)_3$, cycloalkyl, aryl or heteroaryl, wherein multiply substituted radicals are taken to mean radicals which are either multiply, for example doubly or trebly, substituted on different atoms or the same atoms, for example trebly on the same C atom, as in the case of $CF_3$ or —$CH_2CF_3$ or at different positions, as in the case of —CH(OH)—CH=$CHCHCl_2$. Multiple substitution can take place with the same substituent or with different substituents. A substituent may optionally also in turn be substituted; thus —O—alkyl also includes inter alia —O—$CH_2$—$CH_2$—O—$CH_2$—$CH_2$—OH.

With respect to "aryl", "heteroaryl" and "cycloalkyl", according to this invention, "singly or multiply substituted" is taken to mean single or multiple, for example double, treble, quadruple or quintuple, substitution of one or more hydrogen atoms of the ring system by F, Cl, Br, I, CN, $NH_2$, NH-alkyl, NH-aryl, NH-heteroaryl, NH-alkyl aryl, NH-alkyl heteroaryl, NH-cycloalkyl, NH-alkyl OH, $N(alkyl)_2$, $N(alkyl\ aryl)_2$, $N(alkyl\ heteroaryl)_2$, $N(cycloalkyl)_2$, $N(alkyl\ OH)_2$, $NO_2$, SH, S-alkyl, S-cycloalkyl, S-aryl, S-heteroaryl, S-alkyl aryl, S-alkyl heteroaryl, S-cycloalkyl, S-alkyl OH, S-alkyl SH, OH, O-alkyl, O-cycloalkyl, O-aryl, O-heteroaryl, O-alkyl aryl, O-alkyl heteroaryl, O-cycloalkyl, O-alkyl OH, CHO, $C(=O)C_{1-6}$ alkyl, $C(=S)C_{1-6}$ alkyl, $C(=O)$aryl, $C(=S)$aryl, $C(=O)$—$C_{1-6}$ alkyl aryl, $C(=S)C_{1-6}$ alkyl aryl, $C(=O)$-heteroaryl, $C(=S)$-heteroaryl, $C(=O)$-cycloalkyl, $C(=S)$-cycloalkyl, $CO_2H$, $CO_2$-alkyl, $CO_2$-alkyl-aryl, $C(=O)NH_2$, $C(=O)$NH-alkyl, $C(=O)$NH-aryl, $C(=O)$NH-cycloalkyl, $C(=O)N(alkyl)_2$, $C(=O)N(alkyl\ aryl)_2$, $C(=O)N(alkyl\ heteroaryl)_2$, $C(=O)N(cycloalkyl)_2$, S(O)-alkyl, S(O)-aryl, $SO_2$-alkyl, $SO_2$-aryl, $SO_2NH_2$, $SO_3H$, $CF_3$, =O, =S, alkyl, cycloalkyl, aryl and/or heteroaryl, on one atom or optionally on different atoms (wherein a substituent can, in turn, optionally be substituted). Multiple substitution takes place here using the same or different substituents.

The term salt is taken to mean any form of the active ingredient according to the invention in which it assumes or is charged with an ionic form and is coupled to a counter ion (a cation or an anion) or is in solution. This also includes complexes of the active ingredient with other molecules and ions, in particular complexes complexed by ionic interactions. In particular this is taken to mean (and this is also a preferred embodiment of this invention) physiologically acceptable salts, in particular physiologically acceptable salts with cations or bases and physiologically acceptable salts comprising anions or acids or even a salt formed with a physiologically acceptable acid or a physiologically acceptable cation.

The term physiologically acceptable salts with anions or acids is taken to mean, according to this invention, salts of at least one of the compounds of the invention—usually protonated, for example on nitrogen—as cation with at least one anion, which are physiologically acceptable—in particular when applied to humans and/or mammals. In particular, according to this invention, this is taken to mean the salt formed with a physiologically acceptable acid, namely salts of the respective active ingredient with inorganic or organic acids, which are physiologically acceptable—in particular when applied to humans and/or mammals. Examples of physiologically acceptable salts of specific acids are salts of: hydrochloric acid, hydrobromic acid, sulphuric acid, methane sulphonic acid, formic acid, acetic acid, oxalic acid, succinic acid, maleic acid, tartaric acid, mandelic acid, fumaric acid, lactic acid, citric acid, glutamic acid, saccharic acid, monomethyl sebacic acid, 5-oxo-proline, hexane-1-sulphonic acid, nicotinic acid, 2-, 3- or 4-amino benzoic acid, 2,4,6-trimethyl-benzoic acid, α-lipoic acid, acetyl glycine, phosphoric acid, maleic acid, malonic acid, hippuric acid and/or aspartic acid. Hydrochloride salt, citrate and hemicitrate are particularly preferred.

The term "salt formed with a physiologically acceptable acid", according to this invention, is taken to mean salts of the respective active ingredient with inorganic or organic acids, which are physiologically acceptable—in particular when applied to humans and/or mammals. Hydrochloride and citrate are particularly preferred. Examples of physiologically acceptable acids include: hydrochloric acid, hydrobromic acid, sulphuric acid, methane sulphonic acid, formic acid, acetic acid, oxalic acid, succinic acid, tartaric acid, mandelic acid, fumaric acid, lactic acid, citric acid, glutamic acid, saccharic acid, monomethyl sebacic acid, 5-oxo-proline, hexane-1-sulphonic acid, nicotinic acid, 2-, 3- or 4-amino benzoic acid, 2,4,6-trimethyl benzoic acid, α-lipoic acid, acetylglycine, acetylsalicic acid, hippuric acid and/or aspartic acid.

The term "physiologically acceptable salt with cations or bases" is taken to mean, in the context of this invention, salts of at least one of the compounds according to the invention—usually a (deprotonated) acid—as an anion with at least one, preferably inorganic, cation, which are physiologically acceptable, in particular when applied to humans and/or mammals. The salts of the alkali and alkaline earth metals are preferred, and also ammonium salts, in particular however (mono) or (di)sodium, (mono) or (di)potassium, magnesium or calcium salts.

The term "salt formed with a physiologically acceptable with cation" is taken to mean, according to this invention, salts of at least one of the respective compounds as an anion with at least one inorganic cation, which are physiologically acceptable, in particular when applied to humans and/or mammals. The salts of the alkali and alkaline earth metals are particularly preferred, as are ammonium salts, in particular (mono) or (di)sodium, (mono) or (di)potassium, magnesium or calcium salts.

In a preferred embodiment of the spirocyclic cyclohexane derivatives according to the invention $R^1$ and $R^2$ independently of one another represent H; saturated or unsaturated, branched or unbranched, singly or multiply substituted or unsubstituted $C_{1-8}$ alkyl;

or the radicals R¹ and R² together form a ring and represent $CH_2CH_2OCH_2CH_2$, $CH_2CH_2NR^{11}CH_2CH_2$ or $(CH_2)_{3-6}$;
wherein R¹¹ represents H; saturated or unsaturated, branched or unbranched, singly or multiply substituted or unsubstituted $C_{1-8}$ alkyl;

Particularly preferred are spirocyclic cyclohexane derivatives, wherein R¹ and R² independently of one another represent $CH_3$ or H, wherein R¹ and R² do not simultaneously represent H.

Also preferred are spirocyclic cyclohexane derivatives, wherein

R³ represents respectively unsubstituted or singly or multiply substituted cyclopentyl, cyclohexyl, phenyl, benzyl, naphthyl, anthracenyl, thiophenyl, benzothiophenyl, furyl, benzofuranyl, benzodioxolanyl, indolyl, indanyl, benzodioxanyl, pyrrolyl, pyridyl, pyrimidyl or pyrazinyl; respectively unsubstituted or singly or multiply substituted $C_{5-6}$ cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bound by a saturated, unbranched $C_{1-2}$ alkyl group;

in particular

R³ represents respectively unsubstituted or singly or multiply substituted phenyl, furyl, thiophenyl, naphthyl, benzyl, benzofuranyl, indolyl, indanyl, benzodioxanyl, benzodioxolanyl, pyridyl, pyrimidyl, pyrazinyl or benzothiophenyl; respectively unsubstituted or singly or multiply substituted phenyl, furyl or thiophenyl bound by a saturated, unbranched $C_{1-2}$ alkyl group;

Particularly preferred are spirocyclic cyclohexane derivatives, wherein R³ represents respectively substituted or unsubstituted phenyl, phenethyl, thiophenyl, pyridyl or benzyl, more preferably phenyl.

Also particularly preferred are spirocyclic cyclohexane derivatives, wherein R³ represents phenyl, unsubstituted or singly or multiply substituted by F, Cl, CN, $OCH_3$, $OCH_2CH_3$, $CH_3$, $CF_3$ or OH, in particular 3-fluorophenyl and 4-fluorophenyl.

Also preferred are spirocyclic cyclohexane derivatives, wherein R⁵ represents H, branched or unbranched, unsubstituted or singly or multiply substituted $C_{1-5}$ alkyl, or $COOR^{13}$ and R⁶ represents H or $C_{1-5}$ alkyl.

Spirocyclic cyclohexane derivatives are also preferred, wherein R⁷, R8, R⁹ and R¹⁰ independently of one another represent H; branched or unbranched, unsubstituted or singly or multiply substituted $C_{1-5}$ alkyl; F, Cl, Br, I, $CF_3$, OH, $OCH_3$, $NH_2$, COOH, $COOCH_3$, $NHCH_3$ or $N(CH_3)_2$ or $NO_2$.

Particularly preferred are spirocyclic cyclohexane derivatives, wherein the radicals R⁵-R¹⁰ represent H.

Most preferred are spirocyclic cyclohexane derivatives from the group comprising N,N-dimethyl-N-{4-phenyl-1',3',4',5'-tetrahydro-spiro[cyclohexane-1,1'-pyrano[4,3-b]indol]-4-yl}amine N,N-dimethyl-N-{4-phenyl-1',3',4',5'-tetrahydro-spiro[cyclohexane-1,1'-pyrano[4,3-b]indol]-4-yl}amine triflate N,N-dimethyl-N-{4-phenyl-1',3',4',5'-tetrahydro-spiro[cyclohexane-1,1'-pyrano[4,3-b]indiol]-4-yl}amine citrate N,N-dimethyl-N-{4-(4-fluorophenyl)-1',3',4',5'-tetrahydrospiro[cyclohexane-1,1'-pyrano[4,3-b]indol]-4-yl}ammonium triflate N,N-dimethyl-N-{4-(3-fluorophenyl)-1',3',4',5'-tetrahydrospiro[cyclohexane-1,1'-pyrano[4,3-b]indol]-4-yl}ammonium triflate N,N-dimethyl-N-{4-phenyl-spiro[cyclohexane-1,4'-1',4'-dihydro-2'H-3'-oxa-9'-thiafluoren]-4-yl}amine N,N-dimethyl-N-{4-phenyl-spiro[cyclohexane-1,4'-1',4'-dihydro-2'H-3'-oxa-9'-thiafluoren]-4-yl}amine triflate N,N-dimethyl-N-{4-(4-fluorophenyl)-spiro[cyclohexane-1,4'-1',4'-dihydro-2'H-3'-oxa-9'-thiafluoren]-4-yl}ammonium triflate N,N-dimethyl-N-{4-(3-fluorophenyl)-spiro[cyclohexane-1,4'-1',4'-dihydro-2'H-3'-oxa-9'-thiafluoren]-4-yl}ammonium triflate N,N-dimethyl-N-{4-phenyl-1',4'-dihydrospiro[cyclohexane-1,4'-2'H-3',9'-dithiafluoren]-4-yl}ammonium methane sulphonate N,N-dimethyl-N-{4-phenyl-1',4'-dihydrospiro[cyclohexane-1,4'-2'H-9'-oxa-3'-thiafluoren]-4-yl}ammonium methane sulphonate N,N-dimethyl-N-{4-pyridine-1',3',4',5'-tetrahydro-spiro[cyclohexane-1,1'-pyrano[4,3-b]indol]-4-yl}amine N,N-dimethyl-N-{4-pyridine-1',3',4',5'-tetrahydro-spiro[cyclohexane-1,1'-pyrano[4,3-b]indol]-4-yl}amine citrate N,N-dimethyl-N-{4-phenyl-1',4'-dihydrospiro[cyclohexane-1,4'-2'H-3 ,9'-dioxafluoren]-4}ammonium methane sulphonate in the form of the racemate; the enantiomers, diastereomers, mixtures of the enantiomers or diastereomers or an individual enantiomer or diastereomer; the bases and/or salts of physiologically acceptable acids or cations.

The substances according to the invention act, for example, on the i-opioid receptor that is relevant in connection with various diseases, so they are suitable as a pharmaceutical active ingredient in a pharmaceutical composition. The invention therefore also relates to pharmaceutical compositions containing at least one spirocyclic cyclohexane derivative according to the invention and optionally suitable additives and/or auxiliary agents and/or optionally further active ingredients.

The pharmaceutical compositions according to the invention optionally contain, in addition to at least one spirocyclic cyclohexane derivative according to the invention, suitable additives and/or auxiliary agents, therefore also excipients, fillers, solvents, diluents, dyes and/or binders and can be administered as liquid pharmaceutical preparations in the form of injection solutions, drops or syrups, as semi-solid pharmaceutical preparations in the form of granules, tablets, pellets, patches, capsules, plasters or aerosols. The choice of auxiliary agents, etc., and the quantities thereof to be used depend on whether the pharmaceutical preparation is to be applied orally, perorally, parenterally, intravenously, intraperitoneally, intradermally, intramuscularly, intranasally, buccally, rectally or topically, for example to the skin, the mucous membranes or the eyes. Preparations in the form of tablets, dragees, capsules, granules, drops, juices and syrups are suitable for oral application, topical and inhalative application solutions, suspensions, easily reconstituted dry preparations and sprays for parenteral application. Spirocyclic cyclohexane derivatives according to the invention in a deposit, in dissolved form or in a plaster, optionally with the addition of agents to promote skin penetration, are suitable percutaneous application preparations. Forms of preparation which can be administered orally or percutaneously can release the spirocyclic cyclohexane derivatives according to the invention slowly. The spirocyclic cyclohexane derivatives according to the invention can also be administered in the form parenteral long-acting repositories such as implants or implanted pumps. In principle, further active ingredients known to the person skilled in the art can be added to the pharmaceutical preparations according to the invention.

The amount of active ingredient to be administered to the patient varies as a function of the weight of the patient, the method of application, the indication and the severity of the illness. Conventionally, 0.00005 to 50 mg/kg, preferably 0.01 to 5 mg/kg of at least one spirocyclic cyclohexane derivative according to the invention are applied.

With all of the above forms of the pharmaceutical compositions according to the invention it is particularly preferred if the pharmaceutical composition contains, in addition to at least one spirocyclic cyclohexane derivative, a further active ingredient, in particular an opioid, preferably a strong opioid, in particular morphine, or an anaesthetic, preferably hexobarbital or halothane.

In a preferred form of the pharmaceutical composition, a spirocyclic cyclohexane derivative contained according to the invention is present as a pure diastereomer and/or enantiomer, as a racemate or as a non-equimolar or equimolar blend of the diastereomers and/or enantiomers.

The μ-opioid receptor, and also the other opioid receptors, have been identified in particular in the event of pain. Accordingly, spirocyclic cyclohexane derivatives according to the invention can be used for producing a pharmaceutical composition for the treatment of pain, in particular acute, neuropathic or chronic pain.

The invention therefore also relates to the use of a spirocyclic cyclohexane derivative according to the invention for producing a pharmaceutical composition for treating pain, in particular acute, visceral, neuropathic or chronic pain.

The invention also relates to the use of a spirocyclic cyclohexane derivative according to the invention for producing a pharmaceutical composition for the treatment of anxiety, stress and stress-related syndromes, depression, epilepsy, Alzheimer's disease, senile dementia, general cognitive dysfunction, learning and memory disorders (as a nootropic), withdrawal symptoms, alcohol and/or drug and/or medicine abuse and/or dependency, sexual dysfunction, cardiovascular diseases, hypotension, hypertension, tinnitus, pruritus, migraine, hearing difficulties, deficient intestinal motility, impaired nutrient absorption, anorexia, obesity, locomotive disorders, diarrhea, cachexia, urinary incontinence or as a muscle relaxant, anti-convulsive or anaesthetic or for co-administration in treatment with an opioid analgesic or anaesthetic, for diuresis or anti-natriuresis, anxiolysis, for modulation of motor activity, for modulation of neurotransmitter release and treatment of neurodegenerative diseases associated therewith, for the treatment of withdrawal symptoms and/or for reducing the addiction potential of opioids.

In this case it may be preferred in one of the present uses if a spirocyclic cyclohexane derivative used is in the form of a pure diastereomer and/or enantiomer, as a racemate or as a non-equimolar or equimolar blend of the diastereomers and/or enantiomers.

The invention also relates to a method for the treatment, in particular in one of said indications, of a non-human mammal or humans, which or who requires treatment of pain, in particular chronic pain, by administration of a therapeutically effective dose of a spirocyclic derivative according to the invention, or of a pharmaceutical preparation according to the invention.

The invention also related to a process for producing the spirocyclic cyclohexane derivatives according to the invention as stated in detail in the following description and examples. Particularly suitable here is a process, hereinafter called the main process, for producing a spirocyclic cyclohexane derivative according to the invention comprising the following steps, wherein X, W, $R^1$, $R^2$, $R^3$, $R^5$, $R^6$, $R^7$, $R^{8,}$ $R^9$ and $R^{10}$ have the meaning given for the compounds according to the invention of formula I, and $R^{01}$ and $R^{02}$ have the meaning given for the compounds according to the invention of formula I for $R^1$ and $R^2$ and in addition, independently of one another, can represent a protective group:

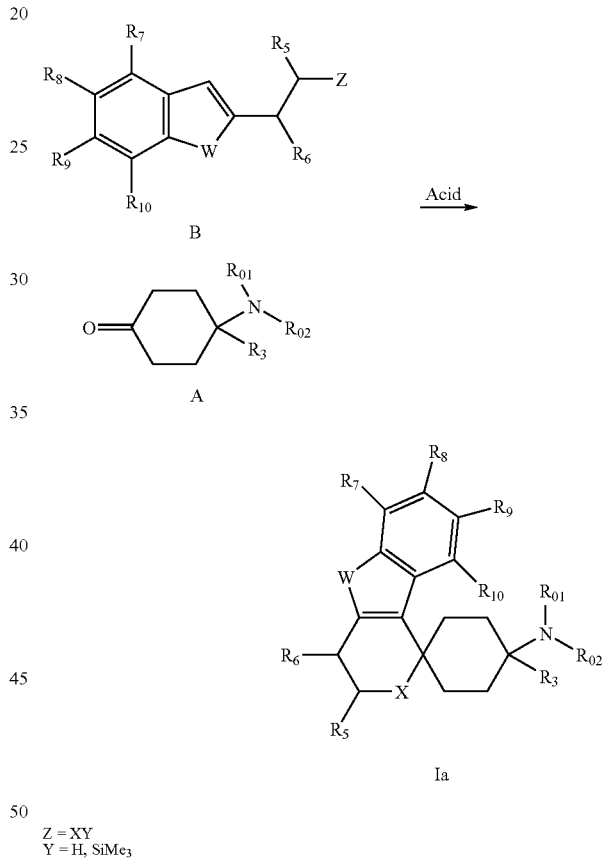

$Z = XY$
$Y = H, SiMe_3$

To produce the compounds of general formula Ia ketones of general formula A are reacted with heteroaromatics of general formula B with addition of acid or trimethylsilylesters thereof, for example trifluoromethanesulphonic acid trimethylsilylester, acetic acid, phosphoric acid, methane sulphonic acid or trifluoroacetic acid in a suitable solvent, for example dichloroethane, dichloromethane, chloroform, acetonitrile, diethyl ether or nitromethane.

Alternatively, production may also take place according to the following pattern, wherein X, W, $R^3$, $R^5$, $R^6$, $R^7$, $R^8$, $R^9$ and $R^{10}$ have the meaning given for compounds according to the invention of formula I, and R$^{01}$ and R$^{02}$ have the meaning given for compounds according to the invention of formula I for R$^1$ and R$^2$ and in addition, independently of one another, can represent a protective group.

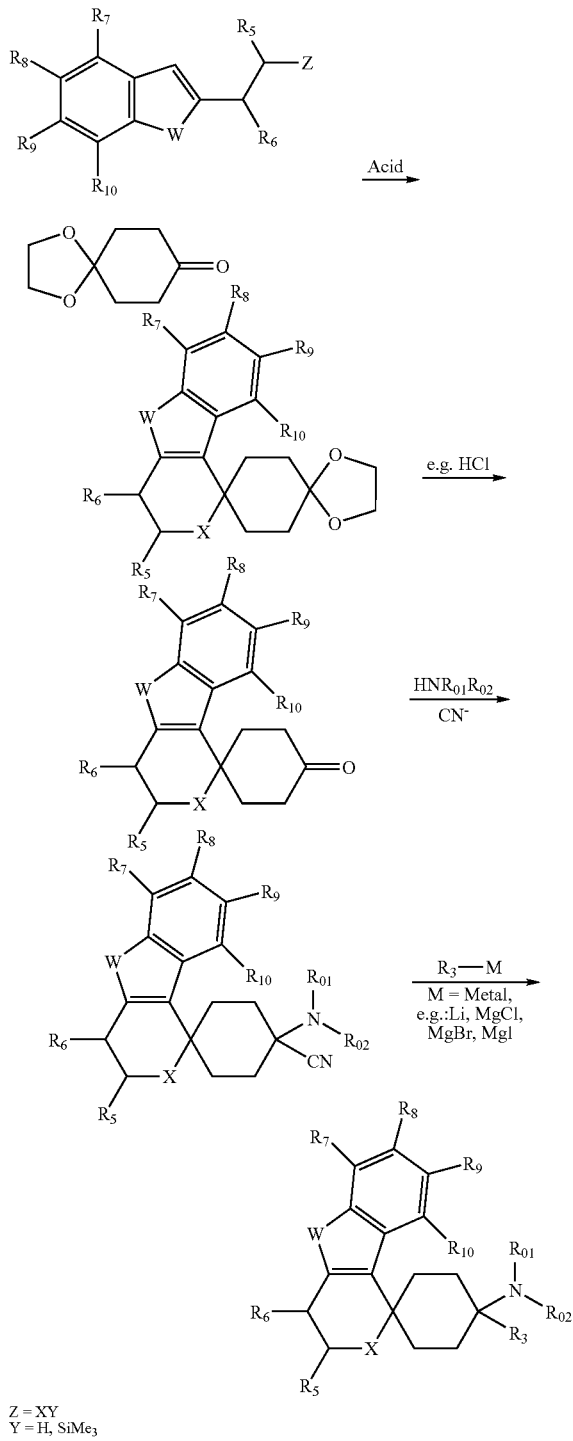

Z = XY
Y = H, SiMe$_3$

Spirocyclic cyclohexane derivates of general formula I, wherein X represents NR$^{17}$ and R$^{17}$ represents COR$^{12}$ or SO$_2$R$^{12}$, can be obtained by the reaction of spirocyclic cyclohexane derivates of general formula I, wherein X represents NH, by reaction with an anhydride or an acid chloride with addition of a base, for example triethylamine. The reaction is preferably carried out with microwave irradiation.

Spirocyclic cyclohexane derivates of general formula I, wherein X represents SO or SO$_2$, can be obtained by reaction of spirocyclic cyclohexane derivates of general formula I, wherein X represents S, with an oxidizing agent, for example H$_2$O$_2$.

EXAMPLES

The following examples are provided to describe certain embodiments of the invention in greater detail, without limiting the invention generally.

The yields of compounds produced have not been optimized.

All temperatures are uncorrected.

The term "ether" denotes diethylether, "EE" ethylacetate and "DCM" dichloromethane. The term "equivalent" denotes equivalent of amount of substance, "mp" melting point or melting range, "decomp." decomposition, "RT" room temperature, "abs." absolute (anhydrous), "rac." racemic, "conc." concentrated, "min" minutes, "h" hours, "d" days, "vol. %" percentage by volume, "m %" percentage by mass and "M" is a concentration in mol/l.

Silica gel 60 (0.040-0.063 mm) from E. Merck, Darmstadt was used as the stationary phase for column chromatography.

The thin-layer chromatography tests were carried out using HPTLC chromatoplates, silica gel 60 F 254, from E. Merck, Darmstadt.

The mixing ratios of mobile solvent for chromatographic tests are always given in volume/volume.

The starting compounds used in the following Examples are either commercially obtainable, or production thereof is known from the prior art or may be derived from the prior art in a manner obvious to a person skilled in the art.

Example 1

N,N-dimethyl-N-{4-phenyl-1',3',4',5'-tetrahydro-spiro[cyclohexane-1,1'-pyrano[4,3-b]indol]-4-yl}amine Example 2

N,N-dimethyl-N-{4-phenyl-1',3',4',5'-tetrahydro-spiro[cyclohexane-1,1'-pyrano[4,3-b]indol]-4-yl}amine triflate Example 3

N,N-dimethyl-N-{4-phenyl-1',3',4',5'-tetrahydro-spiro[cyclohexane-1,1'-pyrano[4,3-b]indol]-4-yl}amine citrate Method A 4-dimethylamino-4-phenyl-cyclohexanone (217 mg, 1 mmol) and 2-(1H-indol-2-yl)ethanol (161 mg, 1 mmol) were dissolved under argon in glacial acetic acid (4 ml) and conc. phosphoric acid (1 ml). The mixture was stirred for 20 h at RT. For working up, the precipitated solid was suction-filtered, suspended in 1N NaOH (30 ml) and stirred for 1 h at room temperature. The spiroether (Example 1) was then suction-filtered in a yield of 61% (200 mg) with a melting point of 311-314° C. as a beige-colored solid.

Method B 4-dimethylamino-4-phenyl-cyclohexanone (217 mg, 1 mmol) together with 2-(1H-indol-2-yl)-ethanol (161 mg, 1 mmol) in absolute dichloromethane (10 ml) were introduced under argon. Trifluoromethane sulphonic acid trimethylsilylester (0.2 ml, 1.03 mmol) was then added. The mixture was stirred for 19 h at RT. For working up, the precipitated triflate was suction-filtered and washed with dichloromethane (2×10 ml). Example 2 was obtained in a yield of 99% (504 mg) as a colorless solid with a melting point of 249-253° C.

Method C

The spiroether obtained by method A (Example 1) (220 mg, 0.61 mmol) was suspended in methanol (100 ml) and mixed with trifluoromethane sulphonic acid (0.11 ml, 1.2 mmol). The reaction mixture was heated for 15 min until reflux, a clear solution being produced. The reaction volume was reduced to 10 ml. After cooling the triflate (Example 2) was suction-filtered in a yield of 70% (217 mg).

Citrate Production

The triflate (Example 2) was suspended in 1N sodium hydroxide solution (15 ml) and stirred for 15 min. The solid obtained was suction-filtered, washed with water (2×10 ml) and dried. The free base (Example 1) was obtained in the process as a beige-colored solid in a yield of 66% (239 mg). To produce the citrate, the base (229 mg, 0.63 mmol) was suspended in methanol (90 ml) at 50° C. and mixed with citric acid (122 mg, 0.63 mmol), dissolved in warm methanol (10 ml). The reaction mixture was stirred for 2 h at RT and the precipitated solid suction-filtered. The citrate (Example 3) was obtained in a yield of 62% (216 mg) as a white solid with a melting point of 249-243° C.

Example 4

N,N-dimethyl-N-{4-(4-fluorophenyl)-1',3',4',5'-tetrahydro-spiro[cyclohexane-1,1'-pyrano[4,3-b]indol]-4-yl}ammonium triflate 4-dimethylamino-4-(4-fluorophenyl)-cyclohexanone (235 mg, 1 mmol) together with 2-(1H-indol-2-yl)-ethanol (161 mg, 1 mmol) was introduced under argon into absolute dichloromethane (10 ml). Trifluorosulphonic acid trimethyisilylester (0.2 ml, 1.03 mmol) was then added. The mixture was stirred for 20 h at RT. For working up, the precipitated triflate was suction-filtered and washed with dichloromethane (2×10 ml). The triflate (Example 4) was obtained in a yield of 94% (495 mg) as a purple-colored solid with a melting point of 232-233° C.

Example 5

N,N-dimethyl-N-{4-(3-fluorophenyl)-1',3',4',5'-tetrahydro-spiro[cyclohexane-1,1'-pyrano[4,3-b]indol]-4-yl}ammonium triflate 4-dimethylamino-4-(3-fluorophenyl)-cyclohexanone (235 mg, 1 mmol) together with 2-(1H-indol-2-yl)-ethanol (161 mg, 1 mmol) was introduced under argon into absolute dichloromethane (10 ml). Trifluoromethane sulphonic acid trimethylsilylester (0.2 ml, 1.03 mmol) was then added. The mixture was stirred for 20 h at RT. For working up, the precipitated triflate was suction-filtered and washed with dichloromethane (2×10 ml). The triflate (Example 5) was obtained in a yield of 98% (518 mg) as a purple-colored solid with a melting point of 174-189° C.

Example 6

N,N-dimethyl-N-{4-phenyl-spiro[cyclohexane-1,4'-1',4'-dihydro-2'H;-3'-oxa-9'-thiafluoren]-4-yl}amine Example 7

N,N-dimethyl-N-{4-phenyl-spiro[cyclohexane-1,4'-1',4'-dihydro-2'H;-3'-oxa-9'-thiafluoren]-4-yl}aminetriflate Method A 4-dimethylamino-4-phenyl-cyclohexanone (217 mg, 1 mmol) and 2-benzyl[b]thiophen-2-yl-ethanol (178 mg, 1 mmol) were dissolved under argon in glacial acetic acid (4 ml) and conc. phosphoric acid (1 ml). The mixture was stirred for 3 d at RT. For working up, the reaction mixture was mixed with ice (30 g) and neutralised with NaHCO$_3$ (9 g, 0.107 mol). After adding diethyl ether (70 ml) the mixture was stirred for 30 min. The organic phase was separated off and the remaining aqueous phase extracted with diethyl ether (2×50 ml). The combined organic extracts were dried over Na$_2$SO$_4$ and concentrated. The residue (386 mg) was separated chromatographically on silica gel (35 g) with ethylacetate/methanol (4:1) and the spiroether (Example 6) isolated in a yield of 14% (53 mg) as a colorless solid with a melting point of 262-263° C.

Method B 4-dimethylamino-4-phenyl-cyclohexanone (217 mg, 1 mmol) together with 2-benzyl[b]thiophen-2-yl-ethanol (178 mg, 1 mmol) was introduced under argon into absolute dichloromethane (10 ml). Trifluoroacetic acid (3 ml) was then added. The mixture was stirred for 24 h at RT. For working up, the reaction mixture was mixed with ice (30 g) and neutralised with NaHCO$_3$ (3.4 g, 0.04 mol. 5N NaOH (0.5 ml) were then added. The aqueous phase was separated off and extracted with dichloromethane (2×30 ml). The combined organic extracts were dried over Na$_2$SO$_4$ and concentrated. The residue (400 mg) was separated chromatographically on silica gel (40 g) with ethylacetate/methanol (4:1) and methanol and the spiroether (Example 6) isolated in a yield of 76% (286 mg) as a colorless solid.

Method C 4-dimethylamino-4-phenyl-cyclohexanone (217 mg, mmol) together with 2-benzyl[b]thiophen-2-yl-ethanol (178 mg, 1 mmol) were dissolved under argon in absolute dichloromethane (5 ml). Methane sulphonic acid (3 ml) was then added. The mixture was stirred for 24 h at RT. For working up, the reaction mixture was mixed with ice (30 g). A colorless solid was precipitated, which was suspended in 1 N sodium hydroxide solution (10 ml) and trichloromethane (30 ml) and stirred for 30 min. The organic phase was separated off and the aqueous phase extracted with trichloromethane (30 ml). The organic extracts were concentrated after drying and the residue (295 mg) separated chromatographically on silica gel (40 g) with ethylacetate/methanol (4:1). The spiroether (Example 6) was isolated in a yield of 35% (102 mg) as a colorless solid.

Method D 4-dimethylamino-4-phenyl-cyclohexanone (217 mg, 1 mmol) together with 2-benzyl[b]thiophen-2-yl-ethanol (178 mg, 1 mmol) were introduced under argon into absolute dichloromethane (10 ml). Trifluorosulphonic acid trimethyisilylester (0.2 ml, 1.03 mmol) was then added. The mixture was stirred for 20 h at RT. For working up, the precipitated triflate suction-filtered and washed with dichloromethane (2×10 ml). The triflate (Example 7) was obtained in a yield of 99% (523 mg) as a colorless solid with a melting point of 209-211° C.

Example 8

N,N-dimethyl-N-{4-(4-fluorophenyl)-spiro[cyclo-hexane-1,4'-1',4'-dihydro-2'H;-3'-oxa-9'-thiafluoren]-4-yl}ammonium triflate 4-dimethylamino-4-(4-fluorophenyl)-cyclohexanone (235 mg, 1 mmol) together with 2-benzyl[b]thiophen-2-yl-ethanol (178 mg, 1 mmol) were introduced under argon into absolute dichloromethane (10 ml). Trifluoromethane sulphonic acid trimethylsilylester (0.2 ml, 1.03 mmol) was then added. The mixture was stirred for 3 d at RT. For working up, the precipitated triflate was suction-filtered and washed with dichloromethane (2×10 ml). The spiroether (Example 8) was obtained in a yield of 97% (527 mg) as a colorless solid with a melting point of 218-221° C.

Example 9

N,N-dimethyl-N-{4-(3-fluorophenyl)-spiro[cyclo-hexane-1.4'-1',4'-dihydro-2'H;-3'-oxa-9'-thiafluoren]-4-yl}ammonium triflate 4-dimethylamino-4-(3-fluorophenyl)-cyclohexanone (235 mg, 1 mmol) together with 2-benzyl[b]thiophen-2-yl-ethanol (178 mg, 1 mmol) was introduced under argon into absolute dichloromethane (10 ml). Trifluoromethane sulphonic acid trimethylsilylester (0.2 ml, 1.03 mmol) was then added. The mixture was stirred for 21 h at RT. For working up, the precipitated triflate was suction-filtered and washed with dichloromethane (2×10 ml). The triflate (Example 9) was obtained in a yield of 90% (492 mg) as a colorless solid with a melting point of 227-231° C.

Example 10

N,N-dimethyl-N-{4-phenyl-1',4'-dihydrospiro[cyclo-hexane-1,4'-2'H;-3',9'-dithiafluoren]-4-yl}ammonium methane sulphate 2-(2-bromethyl)-benzyl[b]thiophene (5.4 g, 21 mmol) was added to a mixture of sodium thiosulphate (6.64 g, 42 mmol), ethanol (70 ml) and water (40 ml) and boiled under reflux for 3.5 h. A clear solution was produced. The reaction solution was evaporated and the residue (colorless solid), which contained corresponding colored salt. The raw product of the colored salt (theoretically 21 mmol) was absorbed in 50% phosphoric acid (130 ml) and dichloromethane (80 ml) and stirred for 80 h at room temperature and for 8 h at 40° C. The reaction mixture was diluted with water (170 ml) and dichloromethane (60 ml) and the phases were separated. The aqueous phase was extracted with dichloromethane (1×50 ml) and the organic phases were combined. The organic phase was washed with water (1×50 ml) then dried and concentrated. 2-benzyl[b]thiophen-2-yl-ethane thiol was obtained as a colorless oil (2.91 g) in a yield of 73%.

4-dimethylamino-4-phenyl-cyclohexanone (217 mg, 1 mmol) together with 2-benzo[b]thiophen-2-ylethanol (194 mg, 1 mmol) were introduced under argon into absolute diethyl ether (8 ml). Methane sulphonic acid (2.8 ml) was then added. A reaction product began to precipitate immediately. The mixture was stirred for 4.5 h at RT. For working up, the precipitated colorless solid was suction-filtered and washed with diethyl ether (2×10 ml). The methane sulphonate (Example 10) was obtained in a yield of 99% (484 mg) and with a melting point of 178-182° C.

Example 11

N,N-dimethyl-N-{4-phenyl-1',4'-dihydrospiro[cyclo-hexane-1,4'-2'H-9'-oxa-3'-thiafluoren]-4-yl}ammonium methane sulphonate A solution of benzyl[b]furan-2-yl-ethanol (2.9 g, 17.9 mmol) in abs. acetonitrile (30 ml) was added dropwise within 10 min and under argon and with water cooling to a suspension of triphenylphosphine dibromide (7.5 g, 17.9 mmol) in dry acetonitrile (20 ml). Toward the end of the addition, a clear solution was produced. The mixture was stirred for 24 h at RT, a solid ($Ph_3PO$) gradually being precipitated. It was suction-filtered and washed with acetone. The filtrate was evaporated on a rotary evaporator. The partially solid residue was mixed with acetone again. $Ph_3PO$ was suction-filtered again and the filtrate evaporated again. The oily residue was purified by chromatography on silica gel G (80 g; cyclohexane). 2-(2-bromethyl)-benzofuran could be obtained in a yield of 81% (3.25 g).

A solution of sodium thiosulphate (4.5 g, 28.6 mmol) and water (50 ml) was added to a mixture of 2-(2-bromethyl)-benzofuran (3.22 g, 14.3 mmol) and ethanol (50 ml). A cloudy solution was produced which became clear on heating. It was heated for 4 h under reflux and then stirred for 18 h at RT. The clear solution was evaporated. To remove impurities the solid residue was mixed with dichloromethane and vigorously stirred for 10 min. It was then suction-filtered and washed with dichloromethane (2×20 ml). The solid obtained was mixed in a 500 ml single-neck flask while stirring with 50% phosphoric acid (85ml) and then with ether (50 ml). After 24 h stirring at RT a three-phase system was produced, to which ether (100 ml) was added. The mixture was heated under reflux for 6 h while stirring, wherein a two-phase system was produced. The phases were separated. The aqueous phase was extracted with diethyl ether (2×50 ml). The combined organic extracts were washed with water (2×50 ml), dried over $Na_2SO_4$ and evaporated after drying. The residue was a yellow oil with solid constituents. The solid was suction-filtered and washed with ether (158 mg, with unknown structure). The filtrate was evaporated. 2-benzofuran-2-yl-ethane thiol was obtained as a light brown oil in a yield of 83% (2.13 g).

4-dimethylamino-4-phenyl-cyclohexanone (217.3 mg, 1 mmol) and 2-benzofuran-2-yl-ethane thiol (178.2 mg, 1 mmol) were dissolved in ether (8 ml) under argon. Methane sulphonic acid (2.8 ml) was added to the clear light brown solution. The solution was stirred for 18 h at RT, then the clear reaction mixture was mixed with ether (40 ml) until clouding occurred. After 1 h the methane sulphonate (Example 11) could be suction-filtered as a white solid with a melting point of 118-142° C. in a yield of 93% (442 mg).

Example 12

N,N-dimethyl-N-{4-pyridine-1',3+,4',5'-tetrahydro-spiro[cyclohexane-1-1'-pyrano[4,3-c]indol]-4-yl}amine

Example 13

N,N-dimethyl-N-{4-pyridine-1',3',4',5'-tetrahydro-spiro[cyclohexane-1-1'-pyrano[4,3-c]indol]-4-yl}amine citrate 4-dimethylamino-4-pyridin-2-yl-cyclohexanone (218 mg, 1 mmol) together with 2-benzyl[b]thiophen-2-ylethanol (178 mg, 1 mmol) were dissolved under argon in absolute dichloromethane (5 ml). Methane sulphonic acid (3 ml) was then added. The mixture was stirred for 3 d at RT. For working up, the reaction mixture was mixed with ice (5 g) and water (30 ml). After neutralisation with NaHCO$_3$ (4.4 g, 52 mmol) and addition of 5N NaOH (1 ml), dichloromethane (10 ml) was added. The organic phase was separated off and the aqueous phase extracted with dichloromethane (2×30 ml). The organic extracts were evaporated after drying and the residue (375 mg) separated chromatographically on silica gel (45 g) with ethylacetate/methanol (10:1), (4:1) and methanol. The spiroether (Example 12) was isolated in a yield of 37% (143 mg) as a colorless solid with a melting point of 155-168° C.

To produce the citrate (Example 13), the base (Example 12) (143 mg, 0.377 mmol) was dissolved in ethanol (10 ml) at 50° C. and mixed with citric acid (72 mg, 0.377 mmol), dissolved in warm ethanol (3 ml). The reaction mixture was stirred for 2 h at RT and concentrated to 5 ml. The solid precipitated in the process was suction-filtered and washed with ethanol (2×1 ml). The citrate was obtained in a yield of 83% (179 mg) as a colorless solid with a melting point of 189-191° C.

Example 14

N,N-dimethyl-N-{4-phenyl-1',4'-dihydrospiro[cyclohexane-1,4'-2'H-3',9'-dioxafluoren]-4-yl}ammonium methane sulphonate 4-dimethylamino-4-phenyl-cyclohexanone (217 mg, 1 mmol) together with 2-benzofuran-2-yl-ethanol (162.2 mg, 1 mmol) were introduced into absolute dichloromethane (10 ml) under argon. Methane sulphonic acid trimethylsilylester (841.5 mg, 5 mmol) was then added. The mixture was stirred for 24 h at RT. Methane sulphonic acid trimethylsilylester was added again (336.6 mg, 2 mmol) and stirred for a further 6 h. For working up, the clear brown solution was mixed with ice (5 g). After a short time a solid had precipitated which was suction-filtered and washed with water (2×10 ml). The methane sulphonate (Example 14) was obtained in a yield of 67% (308 mg) as a colorless solid with a melting point of 249-253° C.

Tests on the Efficacy of the Compounds According to the Invention:

Measurement of the ORL1 Bond

The cyclohexane derivatives of general formula I were investigated in a receptor-binding assay with $^3$H-nociceptin/orphanin FQ with membranes of recombinant CHO-ORL1 cells. This test system was carried out by the method presented by Ardati et al. (Mol. Pharmacol. 51, 1997, p. 816-824). The concentration of $^3$H-nociceptin/orphanin FQ was 0.5 nM in these tests. The binding assays were carried out with 20 pg membrane protein per 200 µl mixture 50 mM Hepes, pH 7.4, 10 mM MgCl$_2$ and 1 mM EDTA. The bond with the ORL1 receptor was determined by using 1 mg WGA-SPA beads (Amersham-Pharmacia, Freiburg), by incubation of the mixture for one hour at RT and subsequent measurement in the Trilux scintillation counter (Wallac, Finland) The affinity is shown in Table 1 as a nanomolar K$_i$ value in or % inhibition at c=1 µM.

By way of example, a value of 49% inhibition at a test concentration of 1 µM was ascertained for Example 13.

Measurement of the µ-Bond

The receptor affinity for the human µ-opiate receptor was determined in a homogeneous mixture in microtiter plates. For this purpose, dilution series of the respective substituted spirocyclic cyclohexane derivative to be tested were incubated with a receptor membrane preparation (15-40 µg protein per 250 µl incubation mixture) of CHO-K1 cells, which express the human µ-opiate receptor (RB-HOM receptor membrane preparation from NEN, Zaventem, Belgium) in the presence of 1 nmol/l of the radioactive ligand [$^3$H]-Naloxon (NET719, NEN, Zaventem, Belgium) and 1 mg WGA-SPA-beads (Wheat germ agglutinin SPA beads from Amersham/Pharmacia, Freiburg, Germany) in a total volume of 250 µl for 90 minutes at room temperature. 50 mmol/l tris-HCl were added as incubation buffer with 0.05% by weight sodium azide and 0.06% by weight bovine serum albumin. 25 µmol/l naloxon were also added to determine the non-specific bond. At the end of the 90 minute incubation period, the microtiter plates were centrifuged off for 20 minutes at 1000 g and the radioactivity measured in a β-counter (Microbeta-Trilux, PerkinElmer Wallac, Freiburg, Germany). The percentage displacement of the radioactive ligand from its bond with the human µ-opiate receptor at a concentration of the test substances of 1 µmol/l was determined and given as a percentage inhibition (% inhibition) of the specific bond. IC$_{50}$ inhibition concentrations, which bring about a 50% displacement of the radioactive ligand, were in some cases calculated by taking as a basis the percentage displacement by various concentrations of the compounds of general formula I to be tested. Ki values for the test substances were obtained by conversion using the Cheng-Prusoff equation.

The following chart provides exemplary bond data:

| Example | % inhibition [1 µM] |
|---------|---------------------|
| 3       | 61                  |
| 7       | 54                  |
| 4       | 62                  |
| 5       | 59                  |
| 13      | 78                  |
| 14      | 60                  |

Binding Site 2 (BTX Bond):

The binding site 2 of the sodium channel is what is known as the batrachotoxin-(BTX) binding site. [$^3$H;]-batrachotoxinin A20 α-benzoate (10 nM in the mixture) wqs used as the ligand. These ion channel particles (synaptosomes) were concentrated from rat cerebrocortex according to Gray and Whittaker (E. G. Gray and V. P. Whittaker (1962) J. Anat. 76, 79-88). The radioactivity measured in the presence of veratridin (0.03 mM in the mixture) is defined as the non-specific bond. Incubation at 25° C. for 120 min. The assay conditions according to the publication by Pauwels, Leysen and Laduron (P. J. Pauwels, J. E. Leysen and P. M. Laduron (1986) Eur. J. Pharmacol. 124, 291-298) were adopted.

The following chart provides exemplary bond data:

| Example | % inhibition [10 μM] |
|---------|----------------------|
| 3 | 76 |
| 7 | 82 |
| 8 | 71 |
| 4 | 64 |
| 5 | 74 |
| 9 | 76 |
| 10 | 75 |
| 11 | 74 |
| 13 | 84 |
| 14 | 86 |

Parental Solution of a Spirocyclic Cyclohexane Derivative According to the Invention 38 g of one of the spirocyclic cyclohexane derivatives according to the invention, Example 3 in this case, were dissolved in 1l water at room temperature for injection purposes and then adjusted to isotonic conditions for injection purposes by adding anhydrous glucose.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A spirocyclic cyclohexane compound corresponding to formula I,

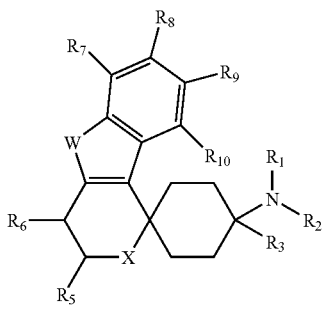

I wherein
$R^1$ and $R^2$ independently of one another represent H; CHO; respectively saturated or unsaturated, branched or unbranched, singly or multiply substituted or unsubstituted $C_{1-5}$ alkyl; respectively saturated or unsaturated, singly or multiply substituted or unsubstituted $C_{3-8}$ cycloalkyl; or respectively singly or multiply substituted or unsubstituted aryl, $C_{3-8}$ cycloalkyl or heteroaryl bound by $C_{1-3}$ alkyl;
or the radicals $R^1$ and $R^2$ together represent $CH_2CH_2OCH_2CH_2$, $CH_2CH_2NR^{11}CH_2CH_2$ or $(CH_2)_{3-6}$;
wherein $R^{11}$ represents H; respectively saturated or unsaturated, branched or unbranched, singly or multiply substituted or unsubstituted $C_{1-5}$ alkyl; respectively saturated or unsaturated, singly or multiply substituted or unsubstituted $C_{3-8}$ cycloalkyl; respectively singly or multiply substituted or unsubstituted aryl or heteroaryl; or respectively singly or multiply substituted or unsubstituted aryl, $C_{3-8}$ cycloalkyl or heteroaryl bound by $C_{1-3}$ alkyl;

$R^3$ represents respectively saturated or unsaturated, branched or unbranched, singly or multiply substituted or unsubstituted $C_{1-5}$ alkyl; respectively saturated or unsaturated, singly or multiply substituted or unsubstituted $C_{3-8}$ cycloalkyl; respectively unsubstituted or singly or multiply substituted aryl or heteroaryl; respectively unsubstituted or singly or multiply substituted aryl, heteroaryl or $C_{3-8}$ cycloalkyl bound by a $C_{1-3}$ alkyl group;

W represents $NR^4$, O or S and $R^4$ represents H; saturated or unsaturated, branched or unbranched, unsubstituted or singly or multiply substituted $C_{1-5}$ alkyl; respectively substituted or unsubstituted aryl or heteroaryl; respectively singly or multiply substituted or unsubstituted aryl, heteroaryl or cycloalkyl bound by a $C_{1-3}$ alkyl group; $COR^{12}$ or $SO_2R^{12}$;
wherein $R^{12}$ represents H; respectively saturated or unsaturated, branched or unbranched, singly or multiply substituted or unsubstituted $C_{1-5}$ alkyl; respectively saturated or unsaturated, singly or multiply substituted or unsubstituted $C_{3-8}$ cycloalkyl; respectively singly or multiply substituted or unsubstituted aryl or heteroaryl; or respectively singly or multiply substituted or unsubstituted aryl, $C_{3-8}$ cycloalkyl or heteroaryl bound by $C_{1-3}$ alkyl; $OR_{13}$ or $NR^{14}R^{15}$;

$R^5$ represents =O; H; $COOR^{13}$, $CONR^{13}$, $OR^{13}$; saturated or unsaturated, branched or unbranched, unsubstituted or singly or multiply substituted $C_{1-5}$ alkyl; saturated or unsaturated, unsubstituted or singly or multiply substituted $C_{3-8}$ cycloalkyl; unsubstituted or singly or multiply substituted aryl or heteroaryl; or unsubstituted or singly or multiply substituted aryl, $C_{3-8}$ cycloalkyl or heteroaryl bound by $C_{1-3}$ alkyl;

$R^6$ represents H; F, Cl, $NO_2$, $CF_3$, $OR^{13}$, $SR^{13}$, $SO_2OR^{13}$, $SO_2OR^{13}$, CN, $COOR^{13}$, $NR^{14}R^{15}$; saturated or unsaturated, branched or unbranched, unsubstituted or singly or multiply substituted $C_{1-5}$ alkyl; saturated or unsaturated, unsubstituted or singly or multiply substituted $C_{3-8}$ cycloalkyl; unsubstituted or singly or multiply substituted aryl or heteroaryl; or unsubstituted or singly or multiply substituted aryl, $C_{3-8}$ cycloalkyl or heteroaryl bound by $C_{1-3}$ alkyl;

or $R^5$ and $R^6$ together represent $(CH_2)n$ where n=2, 3, 4, 5 or 6, wherein individual hydrogen atoms may also be replaced by F, Cl, Br, I, $NO_2$, $CF_3$, $OR^{13}$, CN or $C_{1-5}$ alkyl;

$R^7$, $R^8$, $R^9$ and $R^{10}$ independently of one another represent H, F, Cl, Br, I, $NO_2$, $CF_3$, $OR^{13}$, $SR^{13}$, $SO_2R^{13}$, $SO_2OR^{13}$, CN, $COOR^{13}$, $NR^{14}R^{15}$; unsubstituted or singly or multiply substituted $C_{1-5}$ alkyl, $C_{3-8}$ cycloalkyl; unsubstituted or singly or multiply substituted aryl or heteroaryl; or unsubstituted or singly or multiply substituted aryl, $C_{3-8}$ cycloalkyl or heteroaryl bound by $C_{1-3}$ alkyl;
wherein $R^{13}$ represents H; respectively saturated or unsaturated, branched or unbranched, unsubstituted or singly or multiply substituted $C_{1-5}$ alkyl; respectively saturated or unsaturated, unsubstituted or singly or multiply substituted $C_{3-8}$ cycloalkyl; unsubstituted or singly or multiply substituted aryl or heteroaryl; or unsubstituted or singly or multiply substituted aryl, $C_{3-8}$ cycloalkyl or heteroaryl bound by $C_{1-3}$ alkyl;

$R^{14}$ and $R^{15}$ independently of one another represent H; respectively saturated or unsaturated, branched or unbranched, unsubstituted or singly or multiply substituted $C_{1-5}$ alkyl; or respectively saturated or unsaturated, unsubstituted or singly or multiply substituted $C_{3-8}$ cycloalkyl; unsubstituted or singly or multiply substituted aryl or heteroaryl; or unsubstituted or singly or multiply substituted aryl, $C_{3-8}$ cycloalkyl or heteroaryl bound by $C_{1-3}$ alkyl;

or $R^{14}$ and $R^{15}$ together form $CH_2CH_2OCH_2CH_2$, $CH_2CH_2NR^{16}CH_2CH_2$ or $(CH_2)_{3-6}$;

wherein $R^{16}$ represents H; saturated or unsaturated, branched or unbranched, unsubstituted or singly or multiply substituted $C_{1-5}$ alkyl;

X represents O, S, SO, $SO_2$ or $NR^{17}$;

$R^{17}$ represents H; saturated or unsaturated, branched or unbranched $C_{1-5}$ alkyl; $COR^{12}$ or $SO_2R^{12}$;

or a salt thereof with a physiologically tolerated acid.

2. The compound of claim 1, wherein said compound is present in the form of a free base.

3. The compound of claim 1, wherein said compound is present in the form of a mixture of stereoisomers.

4. The compound of claim 1, wherein said compound is present in the form of a racemic mixture.

5. The compound of claim 1, wherein $R^1$ and $R^2$ independently of one another represent H; saturated or unsaturated, branched or unbranched, singly or multiply substituted or unsubstituted $C_{1-8}$ alkyl; or the radicals $R^1$ and $R^2$ together form a ring and represent $CH_2CH_2OCH_2CH_2$, $CH_2CH_2NR^{11}CH_2CH_2$ or $(CH_2)_{3-6}$, wherein $R^{11}$ represents H; saturated or unsaturated, branched or unbranched, singly or multiply substituted or unsubstituted $C_{1-8}$ alkyl.

6. The compound of claim 1, wherein $R^1$ and $R^2$ independently of one another represent $CH_3$ or H and $R^1$ and $R^2$ do not simultaneously denote H.

7. The compound of claim 1, wherein $R^3$ represents respectively unsubstituted or singly or multiply substituted cyclopentane, cyclohexyl, phenyl, benzyl, naphthyl, anthracenyl, thiophenyl, benzothiophenyl, furyl, benzofuranyl, benzodioxolanyl, indolyl, indanyl, benzodioxanyl, pyrrolyl, pyridyl, pyrimidyl or pyrazinyl; respectively unsubstituted or singly or multiply substituted $C_{5-6}$ cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bound by a saturated, unbranched $C_{1-2}$ alkyl group.

8. The compound of claim 1, wherein $R^3$ represents respectively unsubstituted or singly or multiply substituted phenyl, furyl, thiophenyl, naphthyl, benzyl, benzofuranyl, indolyl, indanyl, benzodioxanyl, benzodioxolanyl, pyridyl, pyrimidyl, pyrazinyl or benzothiophenyl; respectively unsubstituted or singly or multiply substituted phenyl, furyl or thiophenyl bound by a saturated, unbranched $C_{1-2}$ alkyl group.

9. The compound of claim 1, wherein $R^3$ represents respectively substituted or unsubstituted phenyl, phenethyl, thiophenyl, pyridyl or benzyl.

10. The compound of claim 1, wherein $R^3$ represents phenyl.

11. The compound of claim 1, wherein $R^3$ represents phenyl, unsubstituted or singly or multiply substituted by F, Cl, CN, $OCH_3$, $OCH_2CH_3$, $CH_3$, $CF_3$ or OH.

12. The compound of claim 1, wherein $R^3$ represents 3-fluorophenyl or 4-fluorophenyl.

13. The compound of claim 1, wherein $R^5$ represents H, branched or unbranched, unsubstituted or singly or multiply substituted $C_{1-5}$ alkyl or $COOR^{13}$ and $R^6$ represents H or $C_{1-5}$ alkyl.

14. The compound of claim 1, wherein $R^7$, $R^8$, $R^9$ and $R^{10}$ independently of one another represent H; branched or unbranched, unsubstituted or singly or multiply substituted $C_{1-5}$ alkyl; F, Cl, Br, I, $CF_3$, OH, $OCH_3$, $NH_2$, COOH, $COOCH_3$, $NHCH_3$, $N(CH_3)_2$ or $NO_2$.

15. The compound of claim 1, wherein the radicals $R^5$—$R^{10}$ represent H.

16. The compound of claim 1, wherein said compound is selected from the group consisting of:

N,N-dimethyl-N-{4-phenyl-1',3',4',5'-tetrahydro-spiro[cyclohexane-1,1'-pyrano[4,3-b]indol]-4-yl}amine;

N,N-dimethyl-N-{4-phenyl-1',3',4',5'-tetrahydro-spiro[cyclohexane-1,1'-pyrano[4,3-b]indol]-4-yl}amine triflate;

N,N-dimethyl-N-{4-phenyl-1',3',4',5'-tetrahydro-spiro[cyclohexane-1,1'-pyrano[4,3-b]indol]-4-yl}amine citrate;

N,N-dimethyl-N-{4-(4-fluorophenyl)-1',3',4',5'-tetrahydro-spiro[cyclohexane-1,1'-pyrano[4,3-b]indol]-4-yl}ammonium triflate;

N,N-dimethyl-N-{4-(3-fluorphenyl)-1',3',4',5'-tetrahydro-spiro[cyclohexane-1,1'-pyrano[4,3-b]indol]-4-yl}ammonium triflate;

N,N-dimethyl-N-{4-phenyl-spiro[cyclohexane-1,4'-1',4'-dihydro-2'H-3'-oxa-9'thiafluoren]-4-yl}amine;

N,N-dimethyl-N-{4-phenyl-spiro[cyclohexane-1,4'-1',4'-dihydro-2'H-3'-oxa-9'-thiafluoren]-4-yl}amine triflate;

N,N-dimethyl-N-{4-(4-fluorophenyl)-spiro[cyclohexane-1,4'-1',4'-dihydro-2'H-3'-oxa-9'-thiafluoren]-4-yl}ammonium triflate;

N,N-dimethyl-N-{4-(3-fluorophenyl)-spiro[cyclohexane-1,4'-1',4'-dihydro-2'H-3'-oxa-9'-thiafluoren]-4-yl}ammonium triflate;

N,N-dimethyl-N-{4-phenyl-1',4'-dihydrospiro[cyclohexane-1,4'-2'H-3',9'dithiafluoren]-4-yl }ammonium methane sulphonate;

N,N-dimethyl-N-{4-phenyl-1',4'-dihydrospiro[cyclohexane-1,4'-2'H-9'-oxa-3'-thiafluoren]-4-yl}ammonium methane sulphonate;

N,N-dimethyl-N-{4-pyridine-1',3',4',5'-tetrahydro-spiro[cyclohexane-1,1-pyrano[4,3-b]indol]-4-yl}amine;

N,N-dimethyl-N-{4-pyridine-1',3',4',5'-tetrahydro-spiro[cyclohexane-1,1'-pyrano[4,3-b]indol]-4-yl}amine citrate and N,N-dimethyl-N-{4-phenyl-1',4'-dihydrospiro[cyclohexane-1,4'-2'H-3',9'-dioxafluoren]-4-yl}ammonium methane sulphonate.

17. A process for producing a spirocyclic cyclohexane compound according to claim 1, comprising the step of reacting a compound corresponding to formula A

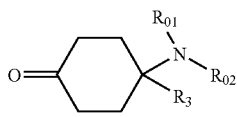

A wherein the radicals $R^{01}$ and $R^{02}$ have the meaning given for $R^2$ and may also represent a protective group, with addition of acid, or the trimethylsilylesters thereof, in a suitable solvent, with a compound corresponding to formula B

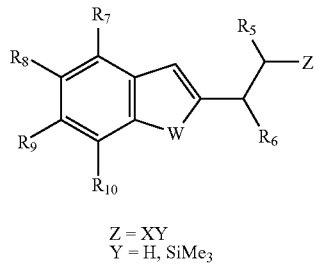

B

18. The process of claim 17, wherein said protective group, with addition of acid, or the trimethylsilylesters thereof, is selected from the group consisting of trifluoromethane sulphonic acid trimethylsilylester, trifluoromethane sulphonic acid, acetic acid, phosphoric acid, methane sulphonic acid and trifluoroacetic acid.

19. The process of claim 17, wherein said solvent is selected from dichloroethane, dichloromethane, chloroform, acetonitrile, diethyl ether and nitromethane.

20. A process for producing a spirocyclic cyclohexane compound according to claim 1, wherein X represents $NR^{17}$ and $R^{17}$ represents $COR^{12}$ or $SO_2R^{12}$, comprising the step of reacting a spirocyclic cyclohexane compound, wherein X represents NH, with the addition of a base, with an anhydride or an acid chloride.

21. The process of claim 20, wherein said base is triethylamine.

22. The process of claim 20, wherein said reacting is performed under microwave irradiation.

23. A process for producing a spirocyclic cyclohexane compound according to claim 1, wherein X represents SO or $SO_2$, comprising the step of oxidizing a spirocyclic cyclohexane compound of formula I wherein X represents S with an oxidizing agent.

24. The process of claim 23, wherein said oxidizing agent is $H_2O_2$.

25. A pharmaceutical composition comprising as an active ingredient a pharmaceutically effective amount of at least one spirocyclic cyclohexane compound according to claim 1 and a pharmaceutically acceptable carrier or adjuvant.

26. The pharmaceutical composition of claim 25, wherein said at least one spirocyclic compound is present in the form of a free base.

27. The pharmaceutical composition of claim 25, wherein said at least one spirocyclic compound is present in the form of a mixture of stereoisomers.

28. The pharmaceutical composition of claim 25, wherein said at least one spirocyclic compound is present in the form of a racemic mixture.

29. The pharmaceutical composition of claim 25, further comprising at least one additional active ingredient which is an opioid or is an anaesthetic selected from the group consisting of hexobarbital and halothane.

30. A method of treating pain in a mammal, said method comprising administering to said mammal an effective pain treating amount of a compound according to claim 1.

31. The method of claim 30, wherein said pain is acute, neuropathic or chronic pain.

* * * * *